(12) United States Patent
Brown et al.

(10) Patent No.: US 6,702,843 B1
(45) Date of Patent: Mar. 9, 2004

(54) STENT DELIVERY MEANS WITH BALLOON RETRACTION MEANS

(75) Inventors: Brian J. Brown, Hanover, MN (US); Anthony C. Vrba, Maple Grove, MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/547,771

(22) Filed: Apr. 12, 2000

(51) Int. Cl.[7] ................................................. A61F 2/06
(52) U.S. Cl. ..................................... 623/1.11; 606/192
(58) Field of Search ...................... 606/1, 108, 192, 606/194, 198, 195; 623/1.1, 1.11, 1.12, 1.18, 1.2, 1.23; 604/96.01, 101.01, 101.02, 101.04, 101.05, 103.05, 103.06, 103.07, 103.08, 103.11, 103.14, 104, 101.03, 915, 917, 919

(56) References Cited

U.S. PATENT DOCUMENTS

| | | | |
|---|---|---|---|
| 4,732,152 A | | 3/1988 | Wallsten et al. ............ 604/271 |
| 4,744,366 A | | 5/1988 | Jang ............................ 128/344 |
| 5,344,426 A | | 9/1994 | Lau et al. .................... 606/198 |
| 5,456,694 A | | 10/1995 | Marin et al. ................. 606/198 |
| 5,534,007 A | | 7/1996 | St. Germain et al. ....... 606/108 |
| 5,571,135 A | * | 11/1996 | Fraser et al. ................. 606/198 |
| 5,628,754 A | | 5/1997 | Shevlin et al. .............. 606/108 |
| 5,632,760 A | | 5/1997 | Sheiban et al. ............. 606/191 |
| 5,634,928 A | | 6/1997 | Fischell et al. ............. 606/108 |
| 5,662,703 A | | 9/1997 | Yurek et al. ................. 606/194 |
| 5,702,364 A | | 12/1997 | Euteneuer et al. ............ 604/96 |
| 5,709,703 A | * | 1/1998 | Lukic et al. ................. 606/198 |
| 5,725,535 A | | 3/1998 | Hegde et al. ................ 606/108 |
| 5,733,299 A | | 3/1998 | Sheiban et al. ............. 606/192 |
| 5,772,669 A | | 6/1998 | Vrba ............................ 606/108 |
| 5,807,398 A | | 9/1998 | Shaknovich ................ 606/108 |
| 5,827,171 A | * | 10/1998 | Dobak et al. ................. 600/16 |
| 5,843,090 A | * | 12/1998 | Schuetz ...................... 623/1.11 |
| 6,004,328 A | * | 12/1999 | Solar .......................... 623/1.11 |
| 6,039,721 A | * | 3/2000 | Johnson et al. .............. 604/508 |
| 6,051,021 A | * | 4/2000 | Frid ............................. 623/12 |
| 6,059,813 A | | 5/2000 | Vrba et al. ................... 606/198 |

FOREIGN PATENT DOCUMENTS

| | | |
|---|---|---|
| EP | 0 917 886 A1 | 5/1999 |
| WO | WO 95/09024 | 4/1995 |
| WO | WO 96/32078 | * 10/1996 |

* cited by examiner

*Primary Examiner*—LoAn H. Thanh
(74) *Attorney, Agent, or Firm*—Vidas, Arrett & Steinkraus PA (57) ABSTRACT

The present invention provides an improved medical device delivery catheter. The medical device delivery system comprises a catheter having a medical device receiving portion adapted to receive a medical device near the distal end of the catheter and a medical device such as a stent concentrically arranged around the catheter within the medical device receiving portion. The medical device delivery system further comprises a movable medical balloon disposed about the medical device. In use, the balloon may be inflated to dilate a lesion, retracted to deploy the medical device and subsequently reinflated to seat the medical device.

30 Claims, 12 Drawing Sheets

STENT DELIVERY MEANS WITH BALLOON RETRACTION MEANS

FIELD OF THE INVENTION

This invention relates to a medical device delivery catheter system, such as the kind used in percutaneous transluminal coronary angioplasty (PTCA) procedures. More particularly, it relates to a medical device delivery catheter employing a movable balloon which is disposed about the medical device.

BACKGROUND OF THE INVENTION

In typical PTCA procedures, a guiding catheter is percutaneously introduced into the cardiovascular system of a patient and advanced through the aorta until the distal end is in the ostium of the desired coronary artery. Using fluoroscopy, a guide wire is then advanced through the guiding catheter and across the site to be treated in the coronary artery. An over the wire (OTW) balloon catheter is advanced over the guide wire to the treatment site. The balloon is then expanded to reopen the artery. The OTW catheter may have a guide wire lumen which is as long as the catheter or it may be a rapid exchange catheter wherein the guide wire lumen is substantially shorter than the catheter. Alternatively, a fixed wire balloon catheter could be used. This device features a guide wire which is affixed to the catheter and cannot be removed. Following dilatation of the vessel, the balloon catheter is removed from the vessel.

To help prevent arterial closure, repair dissection, or prevent restenosis following dilatation, a physician can implant an intravascular prosthesis, or a stent or other such device such as a stent-graft, or a graft, for maintaining vascular patency inside the artery at the lesion. The stent may either be a self-expanding stent or a balloon expandable stent. For the latter type, the stent is often delivered on a balloon and the balloon is used to expand the stent. The self-expanding stents may be made of shape memory materials such as nitinol or constructed of regular metals but of a design which exhibits self expansion characteristics.

In certain known stent delivery catheters, a stent and an optional balloon are positioned at the distal end of the catheter, around a core lumen. The stent and balloon are held down and covered by a sheath or sleeve. When the distal portion is in its desired location of the targeted vessel the sheath or sleeve is retracted to expose the stent. After the sheath is removed, the stent is free to self-expand or be expanded with a balloon.

This multiple step procedure of dilatation with a balloon catheter, removal of the balloon catheter and use of a separate stent delivery catheter is time consuming and requires the use of many different devices. Moreover, the insertion and removal of multiple device increase the opportunity for hemorrhagic complications and increase the overall trauma to the patient. In an effort to reduce the number of insertions and removals of catheters, a number of devices have been disclosed which combine a dilation balloon and a stent delivery catheter in a single device. These devices reflect a variety of approaches.

One approach employs a multiple balloon catheter in which a first balloon is used for dilatation and a second balloon is used for expanding a stent. This approach is disclosed, inter alia, in U.S. Pat. Nos. 5,733,299, 5,632,760, 5,456,694 and 5,725,535.

Another approach employs a balloon which is longitudinally displaceable with respect to the stent. This approach is disclosed, inter alia, in U.S. Pat. No. 5,807,398 and 5,634,928.

The present invention presents another approach to providing a dilatation balloon in a medical device delivery catheter.

For the purpose of this disclosure, the term medical device shall refer to stents, stent-grafts, grafts and vena cava filters.

All U.S. patents and patent applications and all other published documents mentioned anywhere in this application are incorporated herein by reference in their entirety.

BRIEF SUMMARY OF THE INVENTION

The present invention provides an improved medical device delivery system. The medical device delivery system comprises a catheter having an inner tube with a medical device disposed about a receiving region at the distal end thereof and a retractable balloon assembly surrounding at least the medical device. The retractable balloon assembly may comprise a medical balloon in mechanical communication with a balloon retraction device and an inflation lumen in fluid communication with the medical balloon. In one embodiment, the balloon retraction device comprises an outer sheath and an inner sheath. The proximal end of the balloon is attached to the distal end of the outer sheath, and the distal end of the balloon is attached to the distal end of the inner sheath.

The outer sheath of the catheter may include a proximal outer sheath portion and a retractable distal sheath. An optional collapsible sheath may be located between and adhered to the proximal outer sheath and the retractable distal sheath. During retraction of the distal sheath the collapsible sheath collapses upon itself or accordions upon its preformed pleats or creases, providing room for the distal sheath to retract unencumbered, thereby freeing the loaded stent. The inclusion of the collapsible sheath significantly reduces the sheath length, maintains a reduced system profile, provides good flexibility and provides a protective covering to the w ire pull back mechanism.

The outer sheath may also be telescoping. A separate inflation lumen may be provided or the space between an inner and outer sheath may serve as an inflation lumen.

Other objects, features, embodiments and characteristics of the present invention, as well as the methods of operation and functions of the related elements of the structure, and the combination of parts and economics of manufacture, will become more apparent upon consideration of the following description with reference to the accompanying drawings, all of which form a part of this specification.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

Figure 1:
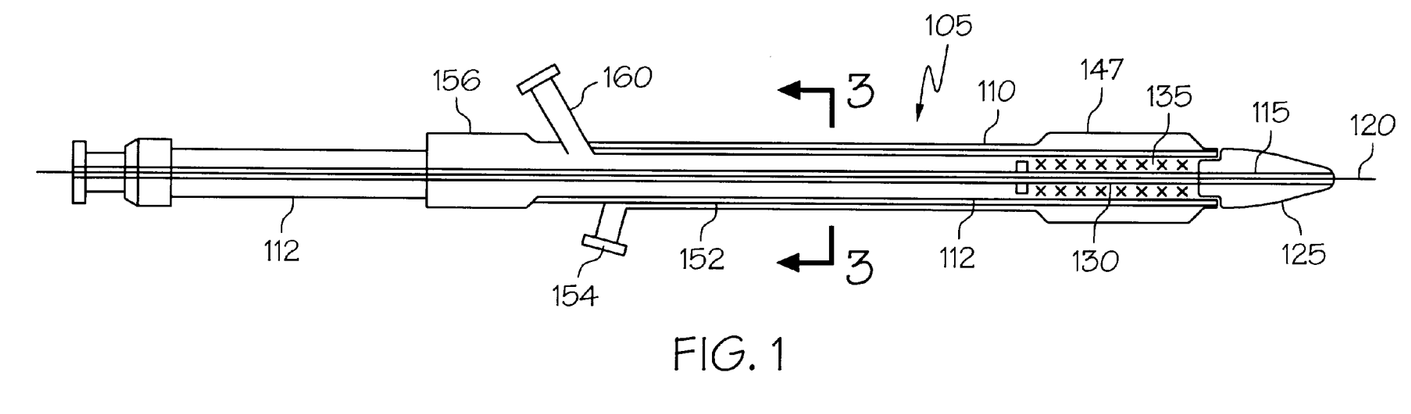
FIG. 1 shows a side view of a catheter according to the invention having a loaded stent including a cross-sectional view of the distal portion thereof and a side view of the proximal end of a catheter according to the invention showing the manifold portion thereof.

FIG. 1 shows a cross-section of the distal portion of a specific embodiment of the stent delivery catheter, generally designated as 105, that is the subject of the present invention. The device generally comprises a proximal outer sheath 110 which covers the majority of the catheter 105 excluding a portion of the distal end of the catheter 105. This outer sheath 110 is characterized by a flexible tube. Preferably the outer sheath 110 is comprised of a high density polyethylene (HDPE) or TEFLON material. The outer sheath 110 is rigidly disposed about an inner sheath 112. Inner sheath 112 encloses an inner tube 115 which also serves as a guide wire lumen. Inner tube 115 extends through and terminates with the distal tip 125 of the catheter 105. Preferably the inner tube 115 encloses a guide wire 120 which aids in the navigation of the catheter 105 through the appropriate vessel. The inner tube 115 is made of flexible, but incompressible construction such as a polymer encapsulated braid or coil. The flexibility of the braid/coil allows the catheter 105 to navigate through body lumens and the incompressibility of the braid/coil aids in maintaining the integrity of the catheter and aids in deployment accuracy when the sheath is being retracted during stent release. The braid/coil may be comprised of stainless steel or nitinol, but preferably stainless steel encased in a polymer such as a polyimide, HDPE, teflon or urethane, but preferably polyimide or teflon.

Figure 2:
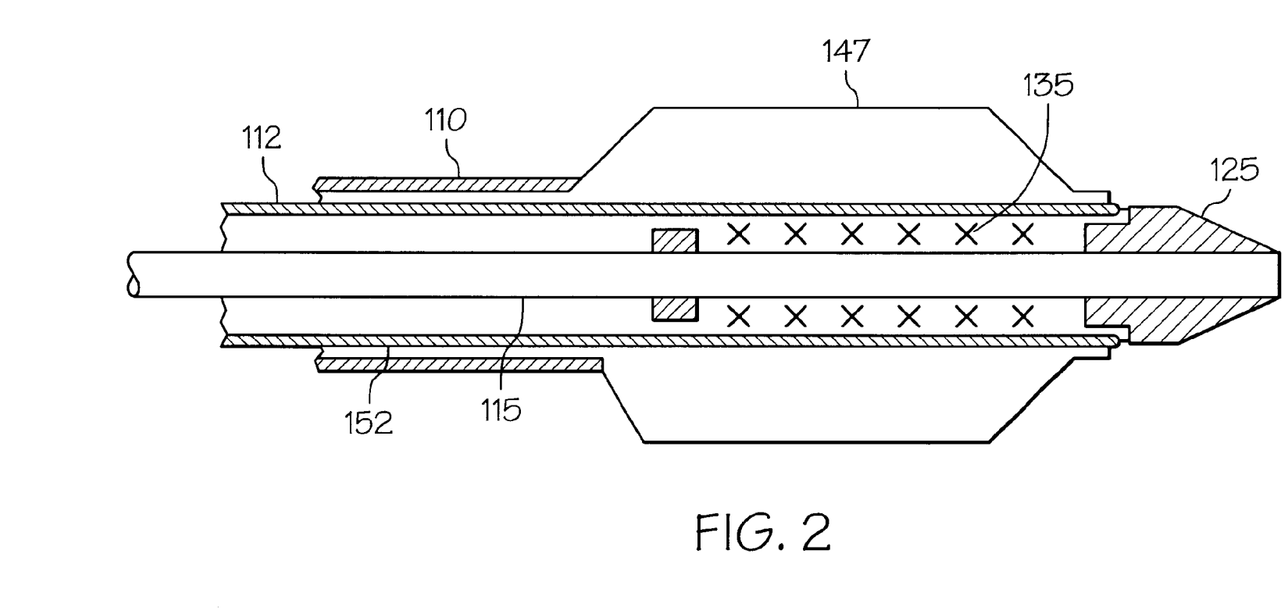
FIG. 2 is an enlarged view of the distal end of the catheter shown in FIG. 1 with a loaded stent.

Situated just proximal to the distal tip 125 is the medical device receiving region 130 of inner tube 115 around which the medical device is concentrically carried. As shown in FIG. 1, the medical device is stent 135. Other medical devices such as stent-grafts, grafts and vena cava filters may also be used. The stent 135 surrounds the inner tube 115. The stent 135 is preferably a Nitinol™ or mesh self-expanding stent, but may also be any other self-expanding stent or a balloon expandable stent carried by an expansion balloon. Self-expanding and balloon expandable stents are well known in the art and require no further instruction. An enlarged view of the distal end of the catheter is shown in FIG. 2.

A medical balloon 147 is disposed about the exterior of inner sheath 112. The distal end of the balloon 147 is connected to the distal end of inner sheath 112. The proximal end of the balloon 147 is connected to the distal end of outer sheath 110. In combination, outer sheath 110, inner sheath 112 and balloon 147 comprise a retractable balloon assembly.

Medical balloon 147 and/or distal end of inner sheath 112 cover and optionally contain the loaded stent 135. The medical balloon 147 and/or distal end of inner sheath 112 may be constructed to hold a self-expanding stent in its reduced delivery configuration. The medical balloon and/or distal end of the inner tube will merely contain a balloon expandable stent. In the case of a balloon expandable stent, the catheter comprises an additional medical balloon located underneath the stent and an accompanying inflation lumen as is well known to those of ordinary skill in the art. Details of such features may be found in commonly assigned U.S. Pat. No. 5,772,669.

Figure 3:
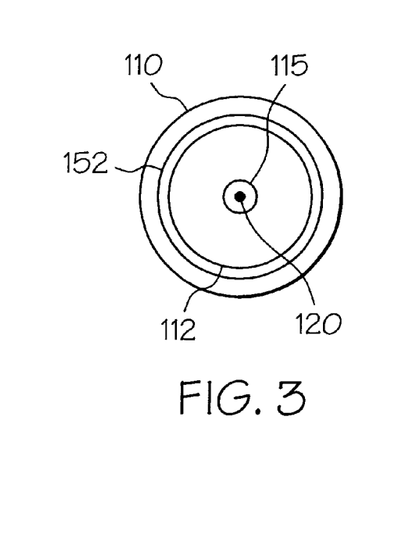
FIG. 3 is a sectional view of the catheter taken along line 3—3 in FIG. 1.

Medical balloon 147 may be used for dilating a vessel as well as for expanding and/or seating a stent. An inflation fluid is supplied to the medical balloon 147 via an inflation lumen 152 which is in fluid communication with the medical balloon. Inflation lumen 152 extends to the proximal end of the catheter where it terminates in balloon inflation port 154. In the instant embodiment, inflation lumen 152 is formed of the space between outer sheath 110 and inner sheath 112, as shown in FIG. 3, a cross-sectional view of catheter 105 of FIG. 1, taken along lines 3—3.

Outer sheath 110 is just short of a full length sheath in that it extends from manifold 156 to the proximal end of balloon 147. Inner sheath 112 is a full length sheath, extending to tip 125 of catheter 105.

Balloon 147 may be made of any suitable balloon material, as known in the art Suitable materials included polyethylene, polyethylene terephthalate (PET), Arnitel, Hytrel, polyetherether ketone (PEEK), Pebax, Teflon as well as other polyolefins. Other thermoplastic elastomers may be used as well. More generally, any suitable thermoplastic elastomer may be used. The invention also contemplates the use of materials suitable for rolling membranes and balloons such as those disclosed in commonly assigned, copending U.S. application Ser. No. 09/187947 filed Nov. 6, 1998, now U.S. Pat. No. 6,059,813, and U.S. Pat. No. 4,732,152.

Figure 4A:
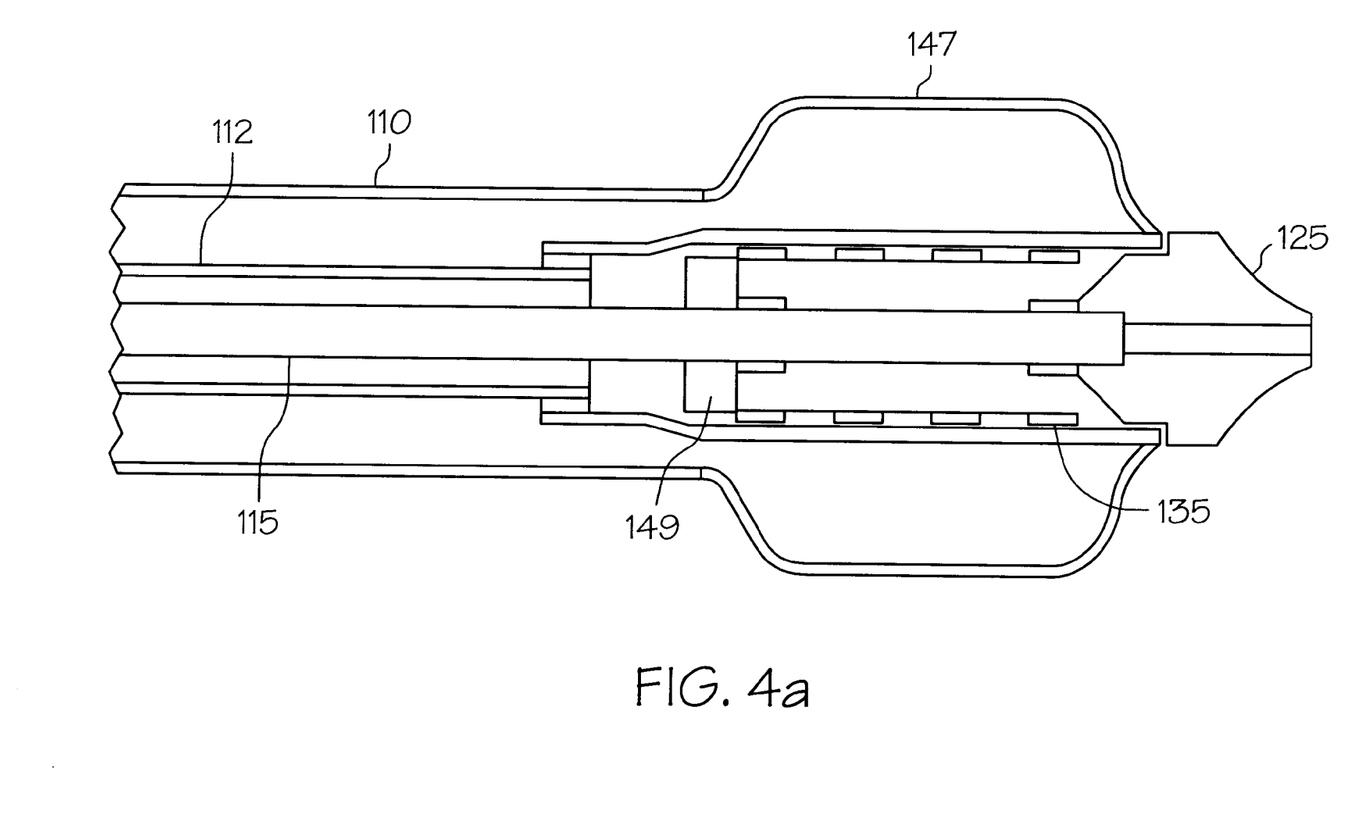
FIG. 4a shows a side view of the distal end of a catheter according to the invention having an axially collapsible balloon and a loaded stent.
Figure 4B:
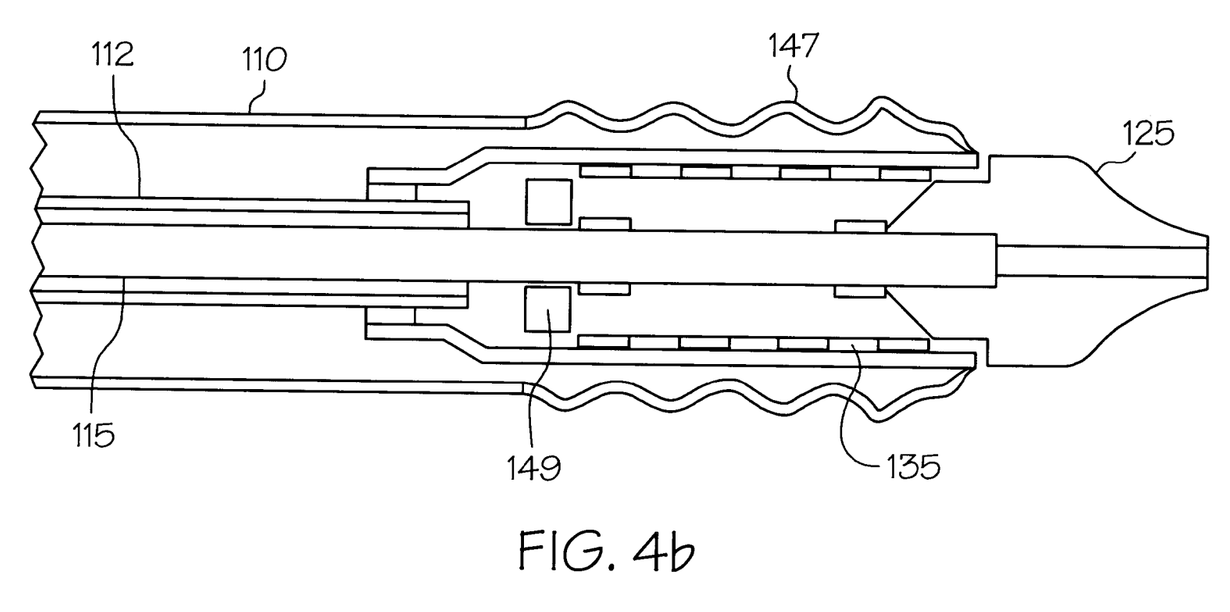
FIG. 4b shows the catheter of FIG. 4a with the balloon partially collapsed.
Figure 4C:
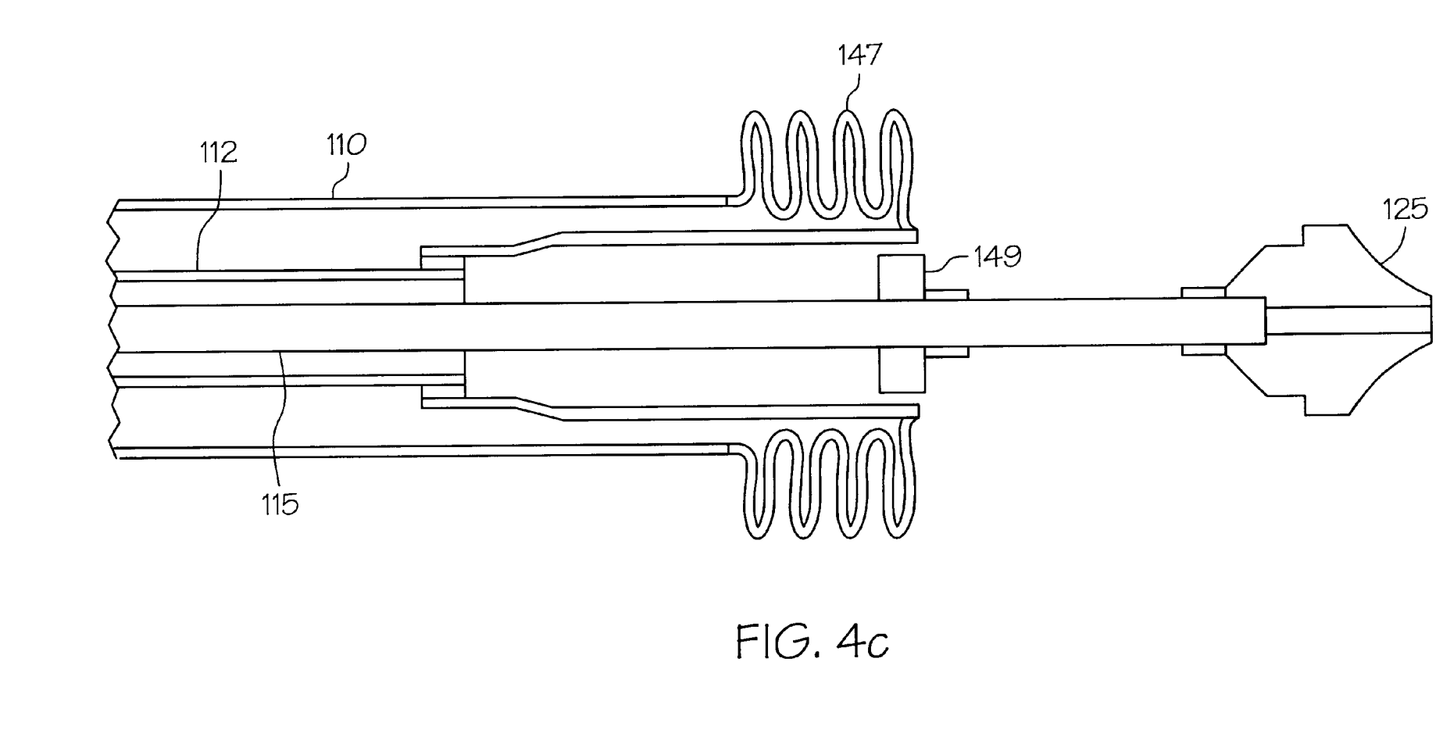
FIG. 4c shows the catheter of FIG. 4a with the balloon fully collapsed.

In an embodiment of the invention shown in FIGS. 4a–c, balloon 147 is pleated so that on movement of inner sheath 112 in a proximal direction, balloon 147 compresses into an accordion-like structure. FIG. 4a shows the catheter with balloon 147 prior to retraction. FIG. 4b shows the catheter as balloon 147 begins to form pleats. When balloon 147 is fully compressed, as shown in FIG. 4c, further motion of inner sheath 112 in a proximal direction results in proximal motion of outer sheath 110 as well. Suitable materials for such a balloon include TEFLON, PEBAX, or LDPE. Balloon 147 covers stent 135 which is disposed about inner tube 115 adjacent to bumpers 149.

Figure 5:
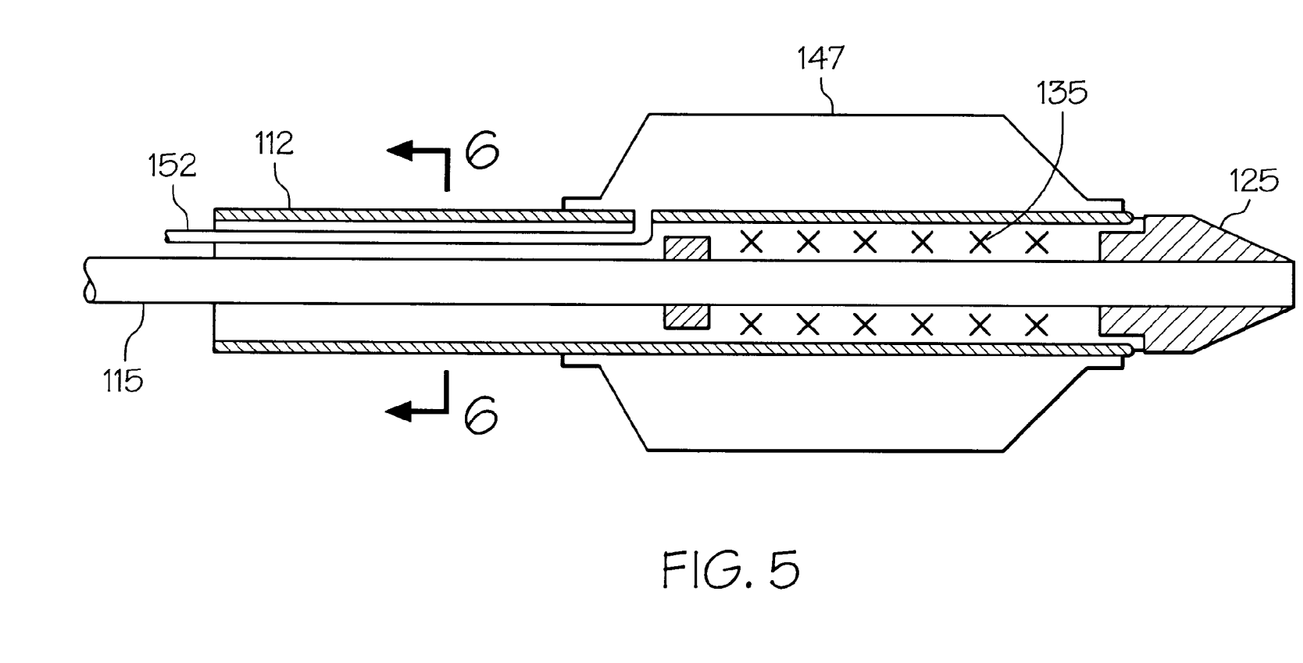
FIG. 5 is a cross sectional view of a distal end of an inventive catheter with a separate tube for an inflation lumen.
Figure 6:
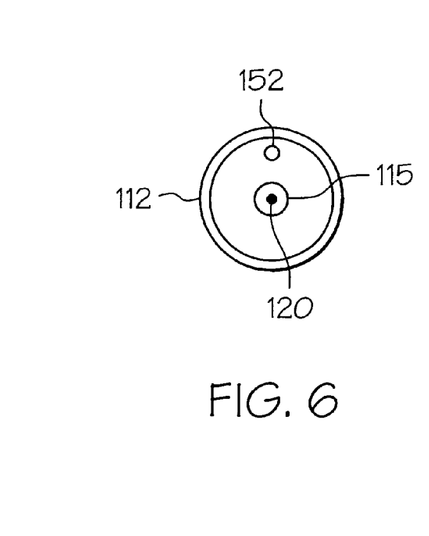
FIG. 6 is a sectional view of the catheter taken along line 6—6 in FIG. 5.

The invention also contemplates embodiments in which a separate tube is provided to serve as an inflation lumen as shown in FIG. 5. Inflation lumen 152 is in fluid communication with balloon 147 and extends to the proximal end of the catheter (not shown) where it is in fluid communication with an inflation port through which inflation fluid is supplied. With the exception of the presence of a separate inflation lumen and the lack of outer sheath 110, the catheter of FIG. 5 is identical in design to that of FIG. 1. The catheter of FIG. 5 is illustrated in cross-sectional view along line 6—6 in FIG. 6.

Figure 7A:
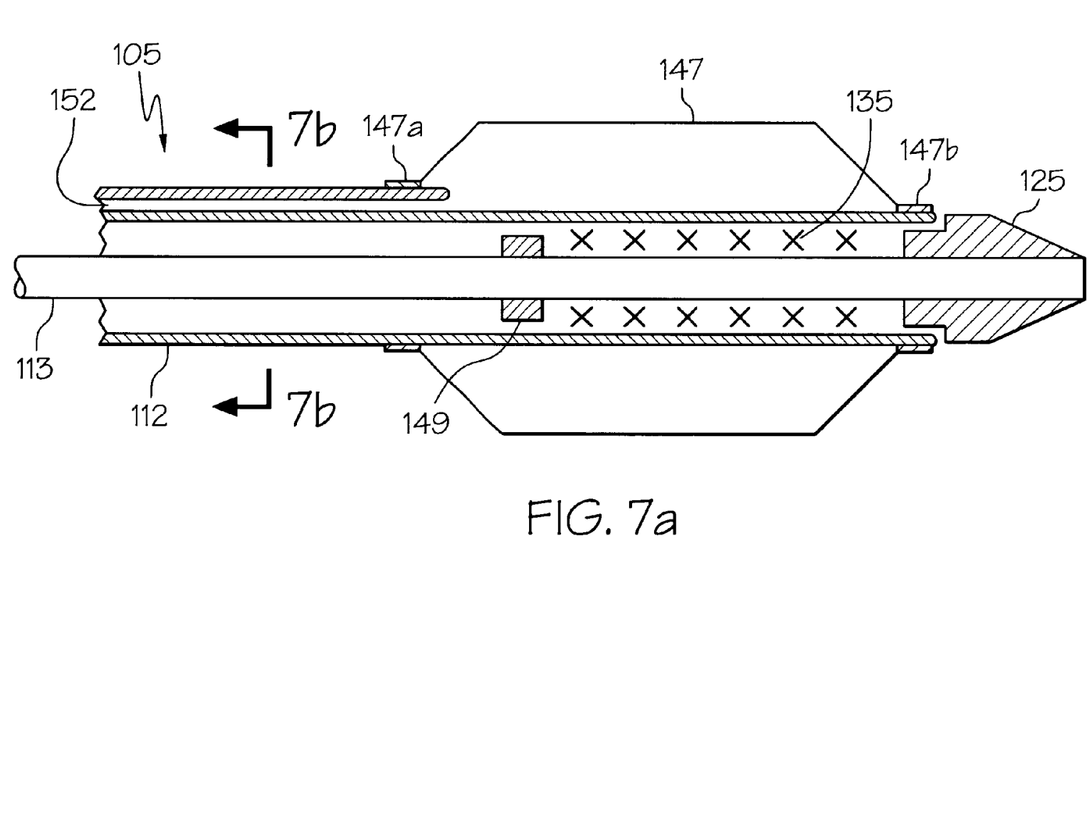
FIG. 7a shows a side view of the distal end of a catheter formed of a dual lumen tube according to the invention.
Figure 7B:
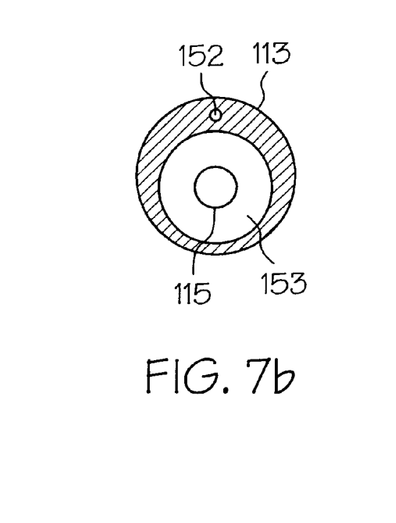
FIG. 7b is a cross sectional view of the catheter of FIG. 7a taken along line 7b—7b.

In another embodiment of the invention, as shown in FIG. 7a, catheter 105 includes a dual lumen tube 113. Dual lumen 113 includes an inflation lumen 152 and an inner tube lumen 153. Inner tube lumen 153 houses inner tube 115. Balloon 147 is mounted on the distal end of dual lumen tube disposed about stent 135. Proximal end 147a and distal end 147b of balloon 147 are mounted to dual lumen tube 113. Balloon 147 is in fluid communication with inflation lumen 152. Stent 135 is disposed about inner tube 115. A transverse view of the catheter, taken along line 7b—7b is shown in FIG. 7b.

Figure 8A:
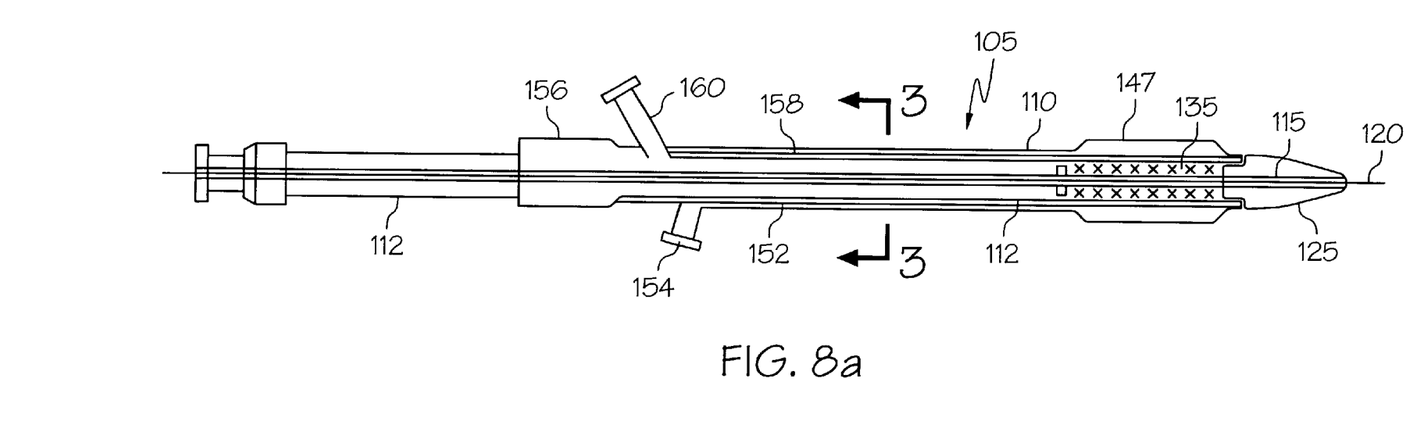
FIG. 8a shows a side view of a catheter according to the invention including a cross-sectional view of the distal portion thereof and a side view of the proximal end of a catheter according to the invention showing the manifold portion thereof.

In yet another embodiment of the invention, outer sheath 110 and inner sheath 112 may be coupled together via a coupling member 158 at a position proximal to balloon 147, as shown in FIG. 8a. In such an embodiment, balloon 147 does not move relative to inner sheath 112 and outer sheath 110. Balloon 147 may then be withdrawn from over the stent by moving one of the inner and outer sheaths in a proximal direction.

The combination of the medical balloon, inner sheath and outer sheath comprises a retractable balloon assembly. In this embodiment, the balloon retraction device is the combination of the inner and outer sheaths.

The catheter further includes a hydrating luer 160 extending from manifold 156.

Figure 8B:
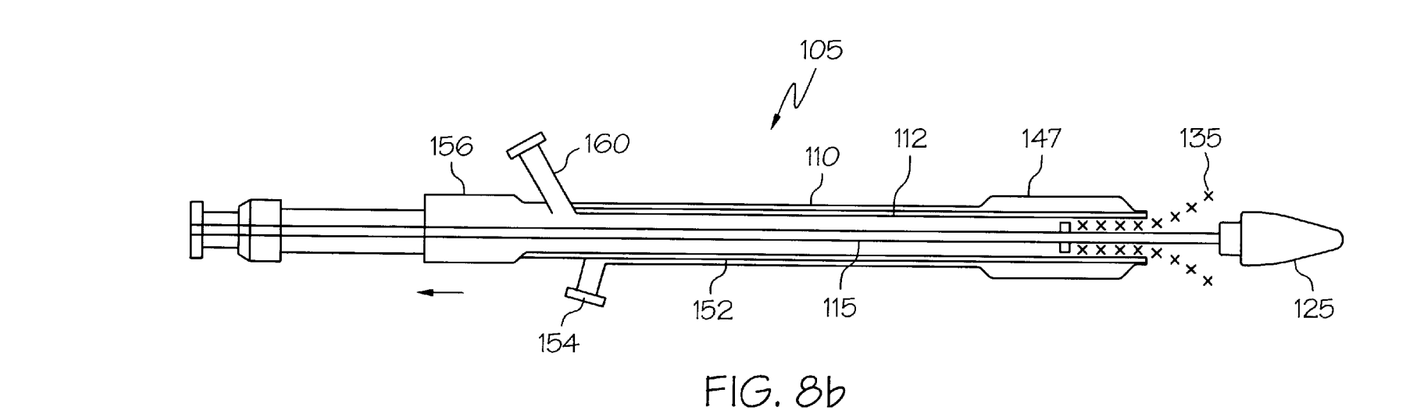
FIG. 8b shows a side view of a catheter according to the invention having a partially deployed stent including a cross-sectional view of the distal portion thereof and a side view of the proximal end of a catheter according to the invention showing the manifold portion thereof.

A catheter similar to that shown in FIG. 8a, with a partially deployed stent is shown in FIG. 8b.

Figure 9:
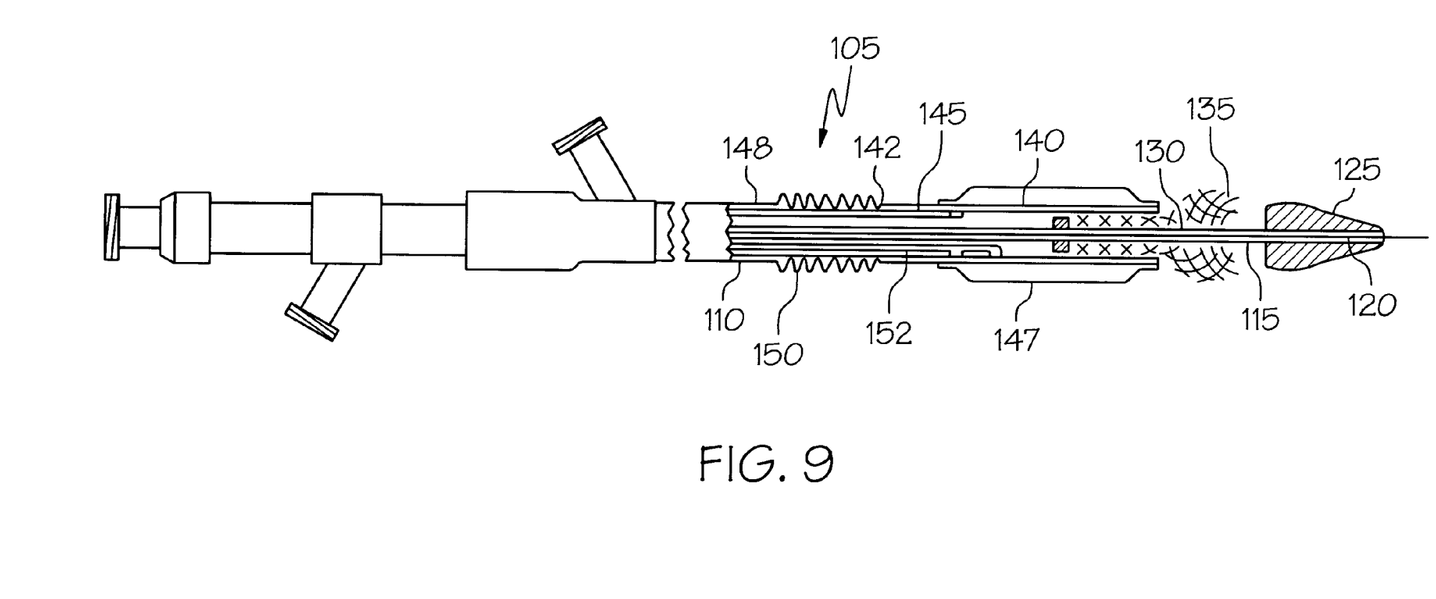
FIG. 9 shows a side view of a catheter according to the invention including a cross-sectional view of the distal portion thereof and a side view of the proximal end of a catheter according to the invention showing the manifold portion thereof.

Another embodiment of the invention is shown in FIG. 9. FIG. 9 shows a partial longitudinal cross-section of the distal portion of a specific embodiment of the stent delivery catheter, generally designated as 105, that is the subject of the present invention. The device generally comprises a proximal outer sheath 110 which covers the majority of the catheter 105 excluding a portion of the distal end of the catheter 105. This outer sheath 110 is characterized by a flexible tube which contains a pull wire lumen and an inflation hydrating lumen. Preferably the outer sheath 110 is comprised of a high density polyethylene (HDPE) or TEFLON material. The proximal outer sheath 110 encloses an inner tube 115 which also serves as a guide wire lumen. Inner tube 115 extends through and terminates with the distal tip 125 of the catheter 105. Preferably the inner tube 115 encloses a guide wire 120 which aids in the navigation of the catheter 105 through the appropriate vessel. The inner tube 115 is made of flexible, but incompressible construction such as a polymer encapsulated braid or coil. The flexibility of the braid/coil allows the catheter 105 to navigate through body lumens and the incompressibility of the braid/coil aids in maintaining the integrity of the catheter and aids in deployment accuracy when the sheath is being retracted during stent release. The braid/coil may be comprised of stainless steel or nitinol, but preferably stainless steel encased in a polymer such as a polyimide, HDPE, teflon or urethane, but preferably polyimide or teflon.

Situated just proximal to the distal tip 125 is the medical device receiving region 130 of inner tube 115 around which the stent is concentrically carried. The stent 135 surrounds the inner tube 115.

The present invention further comprises a retractable distal sheath 140 which covers and optionally contains the loaded stent 135. The retractable distal sheath 140 may be constructed to hold a self-expanding stent in its reduced delivery configuration. The retractable distal sheath will merely contain a balloon expandable stent.

A medical balloon 147 is disposed about at least a portion of the exterior of distal sheath 140. Medical balloon 147 may be used for dilating a vessel as well as for expanding and/or seating a stent. An inflation fluid is supplied to the medical balloon 147 via an inflation lumen 152 which is in fluid communication with the medical balloon. Inflation lumen 152 extends to the proximal end of the catheter.

The distal sheath 140 is connected to a retracting member 145, or pull wire, which allows a physician to retract the distal sheath 140 from the proximal end of the catheter 105, thus releasing the stent 135 in the targeted area of the vessel. The combination of the medical balloon, distal sheath and retracting member 145 comprises a retractable balloon assembly while the retracting member in combination with the distal sheath comprise a balloon retraction device.

The retractable sheath 140 may be flexible or rigid, and is generally used to retain the stent 135 and protect the vessel wall. The distal sheath is preferably formed of a material which provides tensile strength, but is flexible, such as a braid, coil, a super elastic alloy, polymer, stainless steel or other similar composites. The inflation lumen 152 may also be used as a retracting member. The retracting member 145 may also be a rod, a cable, a tube which may also be used to transport fluids, a pull back wire, guide wire or the like, but is preferably a wire. In addition, the retracting member 145 may be tapered along its length to impart varying flexibility. Those skilled in the art will recognize other suitable materials and constructions may be employed to serve substantially the same function. The figure shows a single pull wire. It should be understood that any desired number of pull wires could be utilized. The retracting member 145 extends longitudinally within the proximal outer 110, optionally through a retracting member lumen (not shown), such as a HDPE, nylon, or polyether block amide (PEBAX) tube. In one embodiment, the retracting member lumen extends longitudinally under the proximal outer 110, and houses the pull back wire 145. The retracting member lumen that houses the pull back wire 145 may also carry fluid for purging air from the catheter 105.

The invention additionally comprises a collapsible sheath 150 situated between the proximal outer 110 and the distal sheath 140. The collapsible sheath 150 covers the exposed area between the proximal outer sheath 110 and the distal sheath 140, serving to protect the inner tube 115 and the retracting member 145 in this area. The collapsible sheath 150 is adhered to the proximal end of the distal sheath 140 at point 142 and the distal end of the proximal outer 110 at point 148. These connections between components are preferably made using adhesives such as urethane or cyanoacrylate, and other suitable adhesives that are well known in the art. Connections between polymer components can also be made using other bonding techniques such as thermal welding, ultrasonic welding and the like.

Additional information concerning the manufacture of the collapsible sheath has been disclosed in U.S. Pat. No. 5,534,007.

As the distal sheath 140 is retracted, the collapsible sheath 150 is forced back, collapsing upon itself into an accordion type configuration to give the distal sheath 140 room to retract. The collapsible sheath 150 is longer than the medical device 135 and is made from a highly flexible material such as TEFLON, PEBAX, or LDPE, but preferably TEFLON. The distal sheath 140 and the collapsible sheath 150 may be two separate sheaths adhered to one another, or they may form one continuous sheath.

Further, with the retraction of the distal sheath 140, stent 135 is exposed for deployment. In the case of a self-expanding stent, as shown in FIG. 9, the stent expands upon retraction of the distal sheath.

Figure 10A:
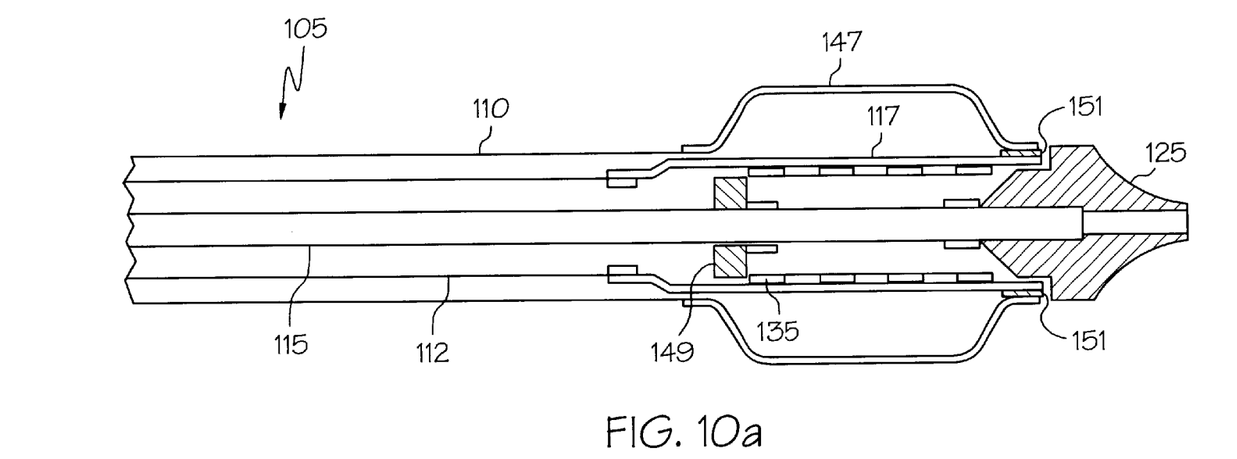
FIG. 10a shows a side view of the distal end of an inventive catheter with a retractable balloon disposed about a stent.
Figure 10B:
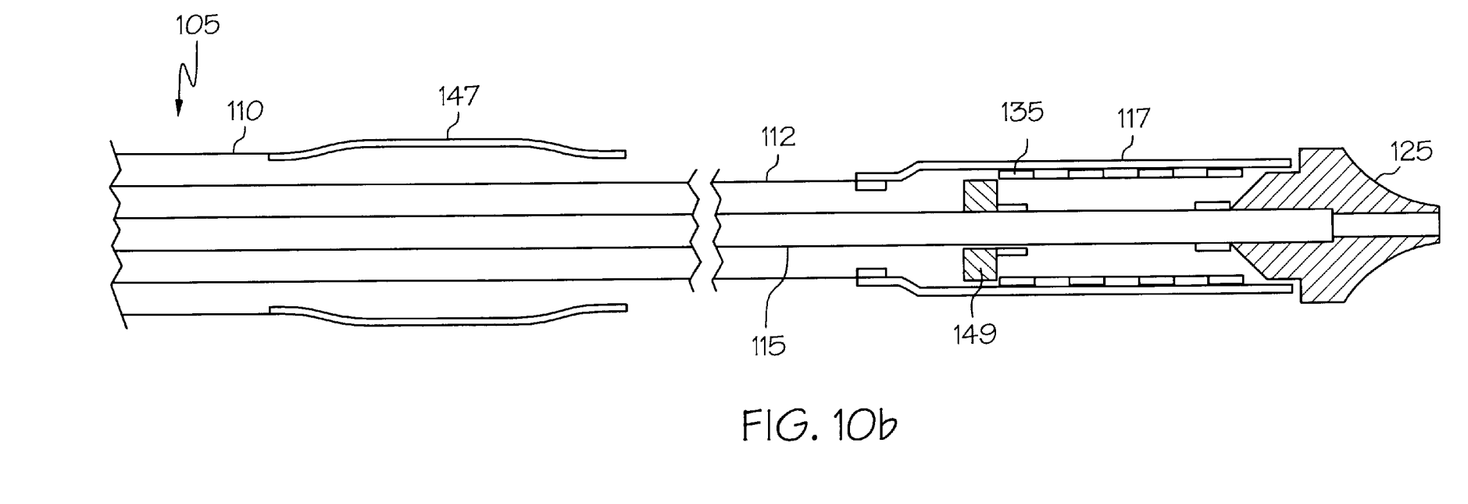
FIG. 10b shows the catheter of FIG. 10a with the balloon retracted.

In yet another embodiment of the invention, catheter 105, as shown in FIG. 10a, includes a retractable balloon 147 disposed about stent 135. Balloon 147 forms the distal end of outer sheath 110. Balloon 147 may be retracted by moving outer sheath 110 in a proximal direction. Stent sheath 117 may be similarly retracted by moving inner sheath 112 in a proximal direction to release the stent for delivery. Catheter 105 is shown in FIG. 10b with balloon 147 retracted and stent sheath 117 covering stent 135. The region between outer sheath 110 and inner sheath 112 defines an inflation lumen 152 for supplying an inflation fluid to balloon 147. Distal end of balloon 147 forms a tolerance seal 151 with distal end of inner sheath 112.

Figure 11A:
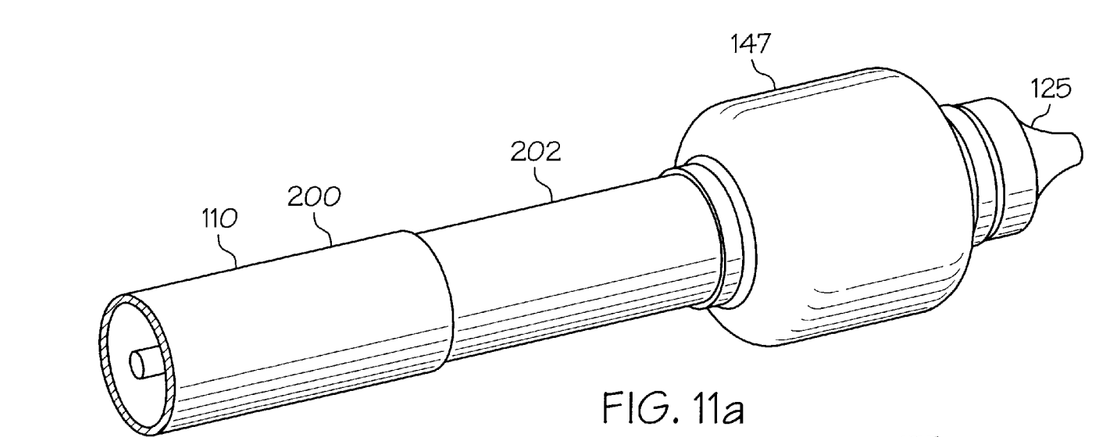
FIG. 11a is a schematic of a telescoping catheter in accordance with the invention.

In a further embodiment as best illustrated by FIG. 11a, the outer sheath 110 is capable of telescopic extension by utilizing outer and inner sheath portions 200, 202 respectively. Outer sheath portion 200 has a diameter greater than that of the inner sheath portion 202. Prior to stent deployment inner sheath portion 202 may extend outward from outer sheath portion 200. When balloon 147 is retracted, inner sheath portion 202 is drawn concentrically into the outer sheath portion 200.

Figure 11B:
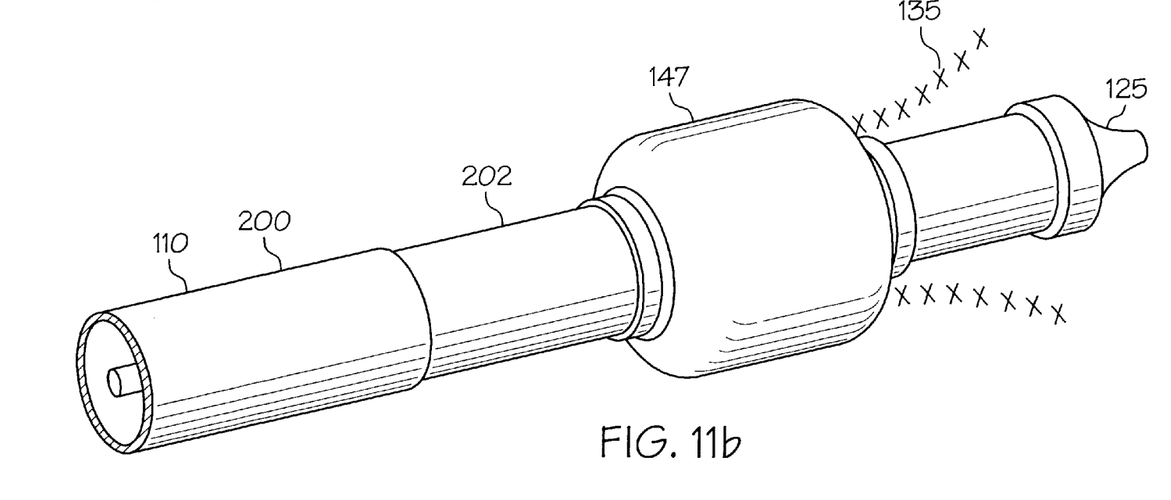
FIG. 11b is a schematic showing the catheter of FIG. 11a after the stent has been partially deployed.

Portion 202 may extend all the way to the proximal end of the catheter or may be movable via a pull wire as rod (not shown) extending to the proximal end of the catheter. FIG. 11b shows a schematic depiction of the catheter of FIG. 11a following retraction of the balloon lumen telescoping portion 202 has been retracted inward into outer sheath portion 200.

In addition to the embodiment shown, a telescopically expandable outer sheath 110 could include additional telescoping portions depending on the diameter of the catheter, the size of the medical device and the amount of extension or retraction required.

Figure 12A:
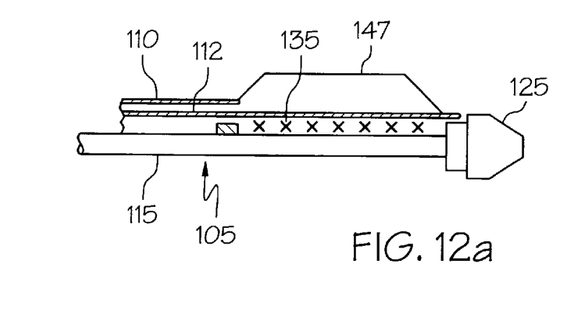
FIG. 12a shows an inventive catheter with a balloon made of a rollable material.
Figure 12B:
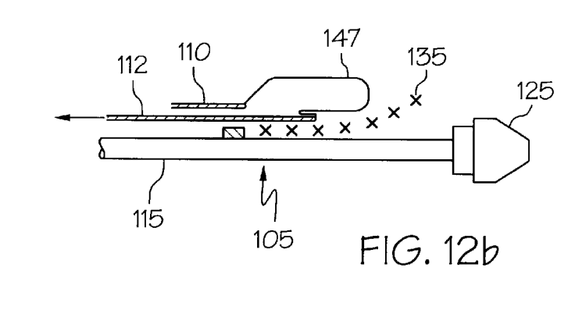
FIG. 12b shows the catheter of FIG. 12a with the balloon partially retracted.
Figure 12C:
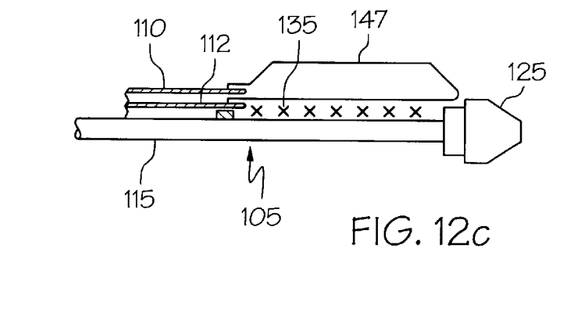
FIG. 12c shows another inventive catheter with a balloon made of a rollable material.
Figure 12D:
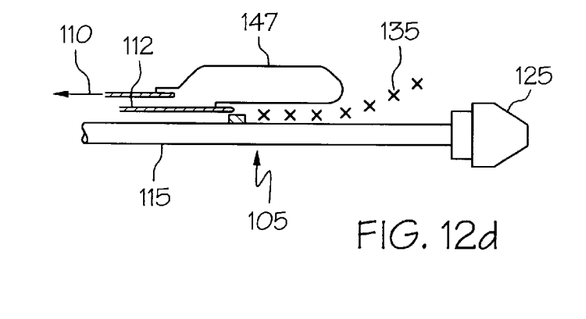
FIG. 12d shows the catheter of FIG. 12c with the balloon partially retracted.

The inventive catheters may also incorporate the use of rollable materials. The operation of several such catheters is shown schematically in FIGS. 12a–f. FIGS. 12a and 12b show a catheter 105 with a balloon 147 made of a rollable material. Balloon 147 may be retracted by moving inner sheath 112 in a proximal direction causing balloon 147 to roll. FIGS. 12c and 12d also show a catheter 105 with a balloon 147 made of a rollable material. Balloon 147 may be retracted by moving outer sheath 110 in a proximal direction causing balloon 147 to roll. On proximal motion of the inner sheath, balloon 147 rolls over on itself until the direction of the balloon has been completely reversed. Further proximal motion of the inner sheath results in proximal motion of the outer sheath as well.

Figure 12E:
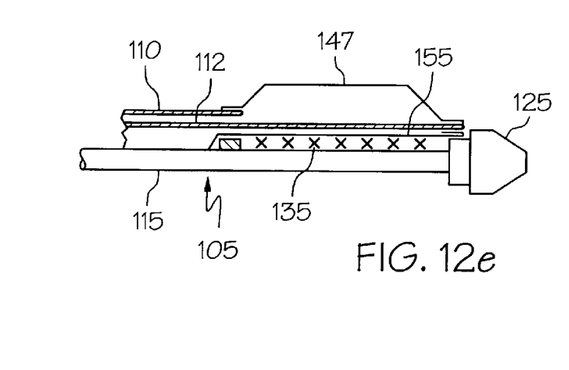
FIG. 12e shows an inventive catheter including a rolling membrane disposed between the balloon and the stent.
Figure 12F:
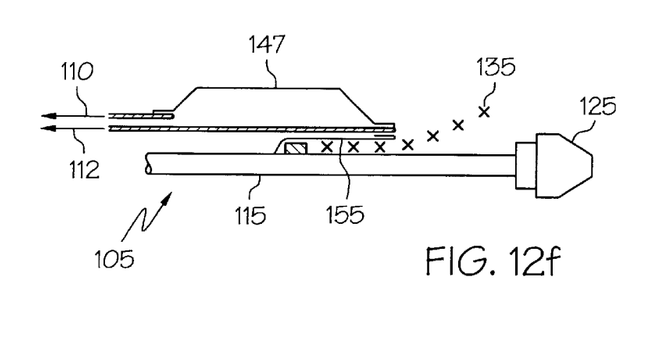
FIG. 12f shows the catheter of FIG. 12e with the balloon partially retracted.

In another embodiment of the invention, as shown in FIG. 12e and 12f, a rolling membrane 155 is attached to the distal end of inner sheath 112. Rolling membrane 155 is situated between inner sheath 112 and stent 135. As inner sheath 112 is retracted, rolling membrane 155 is retracted as well, exposing stent 135.

The inventive catheters may be provided in an over the wire configuration as disclosed above, a fixed wire configuration or a rapid exchange configuration. Suitable features of a fixed wire catheter may be incorporated into the inventive catheter including those features disclosed in commonly assigned U.S. Pat. No. 5,702,364 to Euteneuer et al. Suitable features of a rapid exchange catheter may be incorporated into the inventive including those features disclosed in commonly assigned U.S. Pat. No. 5,534,007 to St. Germain et al.

Although the above description specifically relates to stents, including self-expanding and balloon expandable stents, other medical devices including stent-grafts, grafts and vena cava filters may be delivered using the inventive medical device delivery catheter.

In addition to being directed to the embodiments described above and claimed below, the present invention is further directed to embodiments having different combinations of the dependent features described above and claimed below.

The above disclosure is intended to be illustrative and not exhaustive. This description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A medical device delivery catheter comprising:
    an inner tube with a medical device receiving region at the distal end thereof;
    an expandable medical device disposed about the medical device receiving region, wherein the expandable medical device is not a balloon; and
    an independently expandable retractable balloon assembly surrounding the expandable medical device wherein the independently expandable retractable balloon assembly comprises:
        a medical dilatation balloon in mechanical communication with a balloon retraction device, the medical dilatation balloon being positioned about the expandable medical device;
        an inflation lumen in fluid communication with the medical dilatation balloon; and
        an inner sheath, the inner sheath surrounding at least the expandable medical device, the medical dilatation balloon disposed about the inner sheath.

2. The catheter of claim 1, the medical dilatation balloon having a proximal end and a distal end, wherein the balloon retraction device further comprises:
an outer sheath having a distal end
the proximal end of the medical dilatation balloon attached to the distal end of the outer sheath, and
the distal end of the medical dilatation balloon attached to the distal end of the inner sheath.

3. The catheter of claim 2 wherein
the inner sheath is movable relative to the inner tube; and
the outer sheath is not movable relative to the inner tube.

4. The catheter of claim 3 wherein the medical dilatation balloon is made of a rollable material.

5. The catheter of claim 3 wherein the medical dilatation balloon is collapsible.

6. The catheter of claim 3 wherein the medical dilatation balloon is pleated.

7. The catheter of claim 2 wherein both the outer and the inner sheaths are movable relative to the inner tube, the sheaths interconnected so as to move in unison.

8. The catheter of claim 7 wherein a distal portion of the inner sheath is disposed between the medical dilatation balloon and the expandable medical device.

9. The catheter of claim 2 wherein the outer sheath has a collapsible portion proximal to the medical dilatation balloon and the inner sheath has a pull collar attached thereto, the pull collar distal to the collapsible portion, the pull collar having a pull member extending proximally therefrom.

10. The catheter of claim 9 wherein the pull member is a wire.

11. The catheter of claim 2 wherein the inflation lumen extends between the inner sheath and the outer sheath.

12. The catheter of claim 1 wherein the expandable medical device is selected from the group consisting of stents, stent-grafts grafts and vena cava filters.

13. The catheter of claim 12 wherein the expandable medical device is self-expanding.

14. A method comprising the steps of:
providing a medical device delivery catheter as in claim 13;
inserting the medical device delivery catheter into a bodily vessel;
advancing the medical device delivery catheter such that the medical dilatation balloon is positioned at a desired bodily location;
supplying an inflation fluid to the medical dilatation balloon to expand the medical dilatation balloon and dilate a desired portion of the vessel;
removing at least some of the inflation fluid from the medical dilatation balloon to at least partially deflate the medical dilatation balloon;
retracting the medical dilatation balloon so as to expose the expandable medical device to expand;
deploying the expandable medical device; and
withdrawing the catheter from the bodily vessel.

15. The method of claim 14 further comprising the steps of:
positioning the medical dilatation balloon in the deployed expandable medical device;
supplying an inflation fluid to the medical dilatation balloon to expand the medical dilatation balloon, the expanded medical dilatation balloon engaging the expandable medical device and seating the expandable medical device;
removing at least some of the inflation fluid from the medical dilatation balloon to at least partially deflate the medical dilatation balloon.

16. The catheter of claim 1 wherein the inflation lumen is in fluid communication with the medical dilatation balloon, the inflation lumen extending proximally from the medical dilatation balloon and substantially between the sheath and the inner tube.

17. The catheter of claim 1 further comprising a sheath, the sheath having at least two portions, the at least two portions including an outer portion and an inner portion, the diameter of the outer portion exceeding the diameter of the inner portion, the inner portion slidingly disposed within the outer portion, the medical dilatation balloon disposed about the distal end of the sheath.

18. The catheter of claim 1, wherein the independently expandable retractable balloon assembly is independently expandable when it is in a position in which it at least partially surrounds the expandable medical device.

19. A medical device delivery catheter comprising:
an inner tube, the inner tube having a distal end region;
an expandable medical device disposed about the distal end region of the inner tube;
an inner sheath disposed about at least a portion of the inner tube;
an outer sheath disposed about at least a portion of the inner sheath the inner sheath movable relative to the inner tube;
a retractable medical balloon disposed about the expandable medical device, the retractable medical balloon being retractable so as to expose the expandable medical device,
the retractable medical balloon having a proximal end and a distal end,
the proximal end of the retractable medical balloon connected to a distal part of the outer sheath, and
the distal end of the retractable medical balloon connected to a distal part of the inner sheath,
wherein the retractable medical balloon is retracted by moving the inner sheath in a proximal direction relative to the inner tube.

20. The catheter of claim 19 wherein both the inner sheath and the outer sheath are interconnected such that they move in unison.

21. The catheter of claim 19 wherein the retractable medical balloon is made of a rollable material.

22. The catheter of claim 19 wherein the expandable medical device is selected from the group consisting of stents, stent-grafts, grafts and vena cava filters.

23. The catheter of claim 19 wherein the expandable medical device supportingly engages the retractable medical balloon.

24. The medical device delivery catheter of claim 19, wherein the retractable medical balloon is independently expandable when it is in a position in which it at least partially surrounds the expandable medical device.

25. A medical device delivery catheter having a proximal portion and a distal portion and a longitudinal axis extending along the length of the catheter, the catheter comprising:
a catheter shaft having a distal portion;
a sheath having a distal portion, the sheath and the catheter shaft disposed about the longitudinal axis of the catheter, wherein the sheath is disposed about the catheter shaft;
an inflatable, pleated medical dilatation balloon having a first end connected to the distal portion of the catheter shaft and a second end connected to the sheath;

an inflation lumen, the inflation lumen in fluid communication with the inflatable, pleated medical dilatation balloon, wherein a fluid under pressure can be supplied through the inflation lumen to the inflatable, pleated medical dilatation balloon to expand the inflatable, pleated medical dilatation balloon and wherein a portion of the inflatable, pleated medical dilatation balloon may be moved in a longitudinal direction relative to another portion of the inflatable, pleated medical dilatation balloon; and a stent longitudinally positioned substantially between the first and second ends of the inflatable, pleated medical dilatation balloon, the inflatable, pleated medical dilatation balloon being disposed about the stent.

26. The medical device delivery catheter of claim 25, wherein the inflatable, pleated medical dilatation balloon has a plurality of preformed pleats between the inflatable, pleated medical balloon's first and second ends.

27. The medical device delivery catheter of claim 25, wherein the stent longitudinally positioned substantially between the connection between the first end of the inflatable, pleated medical dilatation balloon and the catheter shaft and the connection between the second end of the inflatable, pleated medical dilatation balloon and the sheath.

28. The medical device delivery catheter of claim 25, wherein the stent is within the catheter shaft.

29. The medical device delivery catheter of claim 25, further comprising an inner catheter shaft disposed within the catheter shaft, wherein the stent is mounting on the inner catheter shaft.

30. The medical device delivery catheter of claim 25, the catheter shaft comprising a proximal shaft having a distal end position proximal to the stent and distal sheath, the distal sheath having a proximal end connected to the distal end of the proximal shaft and a distal end connected to the first end of the inflatable, pleated medical dilatation balloon, wherein the stent is disposed within the distal sheath.

* * * * *